US007304022B2

(12) United States Patent
Cheung et al.

(10) Patent No.: US 7,304,022 B2
(45) Date of Patent: Dec. 4, 2007

(54) CLEANING COMPOSITIONS COMPRISING AN ORGANOSILICONE QUATERNARY AMMONIUM COMPOUND

(75) Inventors: Tak Wai Cheung, Montvale, NJ (US); Edward Fu, Montvale, NJ (US)

(73) Assignee: Reckitt Benckiser Inc., Parsippany, NJ (US)

( * ) Notice: Subject to any disclaimer, the term of this patent is extended or adjusted under 35 U.S.C. 154(b) by 20 days.

(21) Appl. No.: 10/577,093

(22) PCT Filed: Oct. 29, 2004

(86) PCT No.: PCT/GB2004/004591

§ 371 (c)(1),
(2), (4) Date: May 10, 2006

(87) PCT Pub. No.: WO2005/044966

PCT Pub. Date: May 19, 2005

(65) Prior Publication Data

US 2006/0281662 A1    Dec. 14, 2006

(30) Foreign Application Priority Data

Nov. 1, 2003   (GB) ................... 0325565.0

(51) Int. Cl.
*C11D 1/835*   (2006.01)
*C11D 9/36*   (2006.01)
*C11D 3/48*   (2006.01)

(52) U.S. Cl. .............. 510/191; 510/199; 510/466; 510/228; 510/235; 510/238; 510/253; 510/382; 510/384; 510/391; 510/424; 510/426; 510/427; 510/434; 510/473; 510/477; 510/490

(58) Field of Classification Search .............. 510/191, 510/199, 466, 228, 235, 238, 253, 382, 384, 510/391, 424, 426, 427, 434, 473, 477, 490
See application file for complete search history.

(56) References Cited

U.S. PATENT DOCUMENTS

| 5,411,585 | A | 5/1995 | Avery et al. |
| 6,087,319 | A | 7/2000 | Norman |
| 6,087,400 | A * | 7/2000 | Dyer et al. ............ 514/643 |
| 6,239,092 | B1 * | 5/2001 | Papasso et al. ......... 510/238 |
| 6,306,810 | B1 | 10/2001 | Cheung et al. |

FOREIGN PATENT DOCUMENTS

| GB | 2 341 870 A | 3/2000 |
| WO | WO 97/32957 A1 | 9/1997 |
| WO | WO 00/09643 A1 | 2/2000 |

OTHER PUBLICATIONS

International Search Report dated Jan. 11, 2005 for application PCT/GB2004/004591.
Combined Search and Examination Report from The Patent Office in Great Britain dated Mar. 30, 2004 for application GB 0325565.0.
International Preliminary Report on Patentability dated Oct. 17, 2005 for application PCT/GB2004/004591.
Written Opinion of the International Searching Authority for application PCT/GB2004/004591.
Response, dated Aug. 30, 2005, to Written Opinion.

* cited by examiner

*Primary Examiner*—Charles Boyer
(74) *Attorney, Agent, or Firm*—Norris McLaughlin & Marcus, PA

(57) ABSTRACT

Thickened acidic film forming hard surface cleaning and disinfecting compositions which are particularly useful in the cleaning of ceramic surfaces, especially lavatory surfaces.

14 Claims, No Drawings

CLEANING COMPOSITIONS COMPRISING AN ORGANOSILICONE QUATERNARY AMMONIUM COMPOUND

This application is filed under 35 USC 371 of PCT/GB2004/0004591.

The present invention relates to thickened cleaning and disinfecting compositions which are acidic in nature, and which exhibit good cleaning, disinfecting and long term stability. More particularly the present invention provides thickened acidic film forming hard surface cleaning and disinfecting compositions which are particularly useful in the cleaning of ceramic surfaces, especially lavatory surfaces.

While the prior art has provided various compositions directed to cleaning and disinfecting hard surfaces, particularly lavatory surfaces there is yet a continuing need in the art for thickened aqueous compositions which provide: satisfactory cleaning especially of limescale deposits from metal, enamel and porcelain surfaces as found on lavatory fixtures, disinfection of hard surfaces and good long term stability of the thickened compositions. While in many ways effective, these many of these compositions do not provide an appreciable benefit against the buildup of unsightly stains, especially limescale which frequently is most visible at the interface between the surface of water in a toilet bowl, and the inner surface of a toilet bowl.

For example, U.S. Pat. No. 6,239,092 provides a thickened hard surface cleaning composition which features good storage stability and is effective in cleaning of lavatory surfaces, however the compositions do not provide a residual benefit against subsequent buildup of limescale.

The present invention provides stable thickened aqueous acidic hard surface cleaning and disinfecting composition with film forming properties which comprises (preferably consists essentially of):
  one or more nonionic surfactants, particularly linear primary alcohol ethoxylates;
  one or more quaternary ammonium surfactant compounds having germicidal properties;
    an acid constituent based on one or more water soluble organic acids, particularly water soluble organic acids selected from the group consisting of: formic acid, citric acid, mixtures of formic acid with citric acid, and oxalic acid;
    a cellulose based thickening composition;
    a film-forming, organosilicone quaternary ammonium compound;
    optionally but desirably a pH adjusting agent,
    optionally one or more further conventional optional constituents including pH buffering agents, perfumes, perfume carriers, colorants, hydrotropes, fungicides, anti-oxidants, anti-corrosion agents, fragrances, coloring agents;
  and, water.

The inventive compositions exhibit good storage stability, and are at an acidic pH, preferably at a pH of less than about 4.5.

The aqueous acidic hard surface cleaning and disinfecting composition may further include minor amounts, i.e., less than a combined total amount of 10% wt., of conventional additives including but not limited to: colorants such as pigments and dyes; fragrances and perfumes, pH adjusting agents as well as other conventional additives. The compositions of the invention are particularly effective not only in providing a cleaning benefit to against existing soils and stains which are present on hard surfaces, but further provide protection of surfaces treated with the inventive composition against further limescale deposition on such hard surfaces. This effect was particularly noted at the region of the interface of the water in toilets and the interior surface of toilet bowls.

Particularly preferred embodiments of the invention are effective against both gram positive and gram negative bacteria.

The present invention also provides a method for cleaning (especially the removal of limescale deposits) and disinfecting from metal, enamel and porcelain surfaces as found on lavatory fixtures, as well as a method for providing a residual film on surfaces treated with the inventive composition which aids in limiting or preventing further limescale deposition on such hard surfaces The compositions of the invention include one or more nonionic surfactants. These are well known, and any of these are expected to be useful in the inventive compositions. Exemplary useful nonionic surfactants include condensation products of alkylene oxide groups with an organic hydrophobic compound, such as an aliphatic or alkyl aromatic compound. Further exemplary useful nonionic surfactants include the polyoxyethylene ethers of alkyl aromatic hydroxy compounds, e.g., alkylated polyoxyethylene phenols, polyoxyethylene ethers of long chain aliphatic alcohols, the polyoxyethylene ethers of hydrophobic propylene oxide polymers, and the higher alkyl amine oxides. Also contemplated as useful are ethoxylated alkyl phenols such as octylphenolethoxylates and nonylphenolethoxylates.

Preferred nonionic surfactants are ethoxylated alcohols. The compounds are well known and may be formed by condensation of an alcohol, or mixtures thereof, with sufficient ethylene oxide to produce a compound having a polyoxyethylene. Preferably the number of ethylene oxide units are present in an amount sufficient to insure solubility of the compound in an aqueous composition of this invention or in any dilution thereof. Desirably, the ethoxylated alcohols are produced by condensation of about 4-20, more preferably 6-18 moles of ethylene oxide with 1 mole of the linear primary aliphatic alcohol. The aliphatic alcohol may be linear or may be branched, and may be a primary, secondary or tertiary alcohol (including by way of non-limiting example: decyl alcohol, dodecyl alcohol, tridecyl alcohol, hexadecyl alcohol, octadecyl alcohol, and the like). As known to those skilled in the art, the number of moles of ethylene oxide which are condensed with one mole of aliphatic alcohol depends upon the molecular weight of the hydrophobic portion of the condensation product. The aliphatic alcohols are desirably a primary, secondary or tertiary aliphatic alcohol having about 10-20, and preferably 11-17, carbon atoms, and most preferably is an alcohol having 12-16 carbon atoms Especially preferably the nonionic surfactant of the present inventive compositions is the condensation product of linear or branched $C_{12}$-$C_{16}$ aliphatic alcohols, especially $C_{12}$-$C_{16}$ linear aliphatic alcohols or mixtures thereof, with sufficient ethylene oxide to provide an average of from 6-12 moles of ethylene oxide per molecule. Most preferably the nonionic surfactant constituent consists solely of linear or branched $C_{12}$-$C_{16}$ aliphatic alcohols with 6-9 moles of ethylene oxide per molecule.

The nonionic surfactant is present in any effective amount, but generally is present in an amount of up to about 10% by weight, based on the total weight of the composition. Desirably the nonionic surfactant is present in an amount of from about 0.01% wt. to about 10% wt, and most desirably is present in an amount of from about 0.1% wt. to about 10% wt.

The compositions according to the invention include one or more quaternary ammonium surfactant compounds having germicidal properties; these compounds provide a disinfecting effect. Particularly useful quaternary ammonium compounds and salts thereof include quaternary ammonium germicides which may be characterized by the general structural formula:

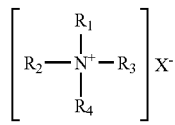

where at least one of $R_1$, $R_2$, $R_3$ and $R_4$ is a hydrophobic, aliphatic, aryl aliphatic or aliphatic aryl radical of from 6 to 26 carbon atoms, and the entire cation portion of the molecule has a molecular weight of at least 165. The hydrophobic radicals may be long-chain alkyl, long-chain alkoxy aryl, long-chain alkyl aryl, halogen-substituted long-chain alkyl aryl, long-chain alkyl phenoxy alkyl, aryl alkyl, etc. The remaining radicals on the nitrogen atoms other than the hydrophobic radicals are substituents of a hydrocarbon structure usually containing a total of no more than 12 carbon atoms. The radicals $R_1$, $R_2$, $R_3$ and $R_4$ may be straight chained or may be branched, but are preferably straight chained, and may include one or more amide or ester linkages. The radical X may be any salt-forming anionic radical.

Exemplary quaternary ammonium salts within the above description include the alkyl ammonium halides such as cetyl trimethyl ammonium bromide, alkyl aryl ammonium halides such as octadecyl dimethyl benzyl ammonium bromide, N-alkyl pyridinium halides such as N-cetyl pyridinium bromide, and the like. Other suitable types of quaternary ammonium salts include those in which the molecule contains either amide or ester linkages such as octyl phenoxy ethoxy ethyl dimethyl benzyl ammonium chloride, N-(laurylcocoaminoformylmethyl)-pyridinium chloride, and the like. Other very effective types of quaternary ammonium compounds which are useful as germicides include those in which the hydrophobic radical is characterized by a substituted aromatic nucleus as in the case of lauryloxyphenyltrimethyl ammonium chloride, cetylaminophenyltrimethyl ammonium methosulfate, dodecylphenyltrimethyl ammonium methosulfate, dodecylbenzyltrimethyl ammonium chloride, chlorinated dodecylbenzyltrimethyl ammonium chloride, and the like.

Preferred quaternary ammonium compounds which act as germicides and which are found useful in the practice of the present invention include those which have the structural formula:

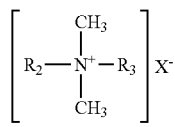

wherein $R_2$ and $R_3$ are the same or different $C_8$-$C_{12}$alkyl, or $R_2$ is $C_{12-16}$alkyl, $C_{8-18}$alkylethoxy, $C_{8-18}$alkylphenolethoxy and $R_3$ is benzyl, and X is a halide, for example chloride, bromide or iodide, or is a methosulfate counterion. The alkyl groups recited in $R_2$ and $R_3$ may be straight chained or branched, but are preferably substantially linear.

Particularly useful quaternary germicides include compositions which include a single quaternary, as well as mixtures of two or more different quaternary. Particularly useful quaternary germicides include BARDAC® 205M, and BARDAC® 208M or BTC® 885 which is described to be a blend of alkyl dimethyl benzyl ammonium chlorides; BARDAC® 2050 and BARDAC® 2080 or BTC® 818 which is described to be based on dialkyl($C_8$-$C_{10}$)dimethyl ammonium chloride; BARDAC® 2250 and BARDAC® 2280 or BTC® 1010 which is described to be a composition which includes didecyl dimethyl ammonium chloride; BARDAC® LF and BARDAC® LF 80 which is described to be based on dioctyl dimethyl ammonium chloride; BARQUAT® MB-50, HYAMINE® 3500, BARQUAT® MB-80, BTC® 835, BTC® 8358 or BTC® 65 USP each described to be based on alkyl dimethyl benzyl ammonium chloride; BARQUAT® MX-50, BARQUAT® MX-80, BTC® 824 or BTC® 8248 each described to be a composition based on alkyl dimethyl benzyl ammonium chloride; BARQUAT® OJ-50, BARQUAT® OJ-80, BTC® 2565, or BTC® 2658 each described to be a composition based on alkyl dimethyl benzyl ammonium chloride; BARQUAT® 4250, BARQUAT® 4280, BARQUAT® 4250Z, BARQUAT® 4280Z, BTC® 2125, or BTC® 2125M each described to be a composition based on alkyl dimethyl benzyl ammonium chloride and/or alkyl dimethyl ethyl benzyl ammonium chloride; BARQUAT® MS-100 or BTC® 324-P-100 each described to be based on myristyl dimethyl benzyl ammonium chloride; HYAMINE® 2389 described to be based on methyl dodecyl benzyl ammonium chloride and/or methyl dodecyl xylene-bis-trimethyl ammonium chloride; HYAMINE® 1622 described to be an aqueous solution of benzethonium chloride; HYAMINE® 3500-NF or BTC® 50 each described to be based on alkyl dimethyl benzyl ammonium chloride; as well as BARQUAT® 1552 or BTC® 776 described to be based on alkyl dimethyl benzyl ammonium chloride and/or dialkyl methyl benzyl ammonium chloride. (Each of these recited materials are presently commercially available from Lonza, Inc., Fairlawn, N.J. and/or from Stepan Co., Northfield Ill.).

These quaternary ammonium surfactant compounds may be present in any effective amount, but and are effective in amounts from as little as 0.001% wt. Typically, these compounds are present in amounts of from 0.01-10% by weight, based on the total weight of the composition. Desirably these compounds are present in amounts from 0.01-7% wt, more desirably from 0.1-5% wt., and most desirably from 0.1-3% wt.

These quaternary ammonium compounds are often provided in an alcohol such as a $C_1$-$C_6$ alcohol (i.e., ethanol, n-propanol, isopropanol, n-butanol, sec-butanol) or in an aqueous/alcohol mixture containing such alcohols. While these alcohols are present in only a very minor amount as they are supplied as part of the quaternary ammonium compounds it is believed they contribute to the antimicrobial efficacy of the invention. Therefore, up to about 1% wt. of a $C_1$-$C_6$ alcohol, preferably 0.001-1% wt., more preferably 0.01-0.75% wt. be present in the inventive compositions if provided with the quaternary ammonium compound.

In the cleaning compositions according to the invention, the quaternary ammonium compound constituent is required to be present in amounts which are effective in exhibiting satisfactory germicidal activity against selected bacteria sought to be treated by the cleaning compositions. Such efficacy may be achieved against less resistant bacterial strains with only minor amounts of the quaternary ammonium compounds being present, while more resistant strains of bacteria require greater amounts of the quaternary ammonium compounds in order to destroy these more resistant strains. The quaternary ammonium compound need only pre present in germicidally effective amounts, but may be present in amounts from 0.01%-10% wt. based on the total weight of the composition of which they form a part. Generally, effective "hospital strength" germicidal efficacy meeting current EPA guidelines is provided when the quaternary ammonium compounds are present in an amount of 0.01-7% wt, more desirably from 0.1-5% wt., and most desirably from 0.1-3% wt. based on the total weight of the inventive compositions being taught herein.

The inventive compositions necessarily comprise an acid constituent based on one or more water soluble organic acids, particularly one or more water soluble organic acids selected from the group consisting of: formic acid, citric acid, mixtures of formic acid with citric acid, and oxalic acid. The acid constituent may be present in any effective amount, but desirably is not present in amounts of more than about 10% wt. based on the total weight of the compositions. Desirably the acid constituent forms from 0.01-20% wt., more desirably from 0.1-15% wt. of the inventive compositions. The water soluble organic acids include at least two carbon atoms, and include at least one carboxyl group (—COOH) in its structure.

As noted, the compositions of the invention are thickened and have a viscosity greater than water. The actual degree of thickening is dependent on the amount of thickener included in a composition. Thickeners which may be used are cellulose based thickeners including but not limited to: methyl cellulose, methylethyl cellulose, hydroxymethyl cellulose, hydroxyethyl cellulose, carboxymethyl cellulose, and the like. Generally the thickener is present in not more than about 10% wt. based on the total weight of the composition of which it forms a part. Desirably the thickener is present in an amount of from 0.01-5% wt., and more desirably from 0.1-5% wt. Starch based thickeners, including so called modified starch based thickeners as frequently encountered in the foods industry are also contemplated as being useful.

The inventive compositions necessarily include a film-forming, organosilicone quaternary ammonium compound. Such compounds may also exhibit antimicrobial activity, especially on hard surfaces which may supplement the effect of the quaternary ammonium surfactant compounds having germicidal properties.

Specific examples of organosilicone quaternary ammonium salts that may be used in the compositions of this invention include organosilicone derivatives of the following ammonium salts: di-isobutylcresoxyethoxyethyl dimethyl benzyl ammonium chloride, di-isobutylphenoxyethoxyethyl dimethyl benzyl ammonium chloride, myristyl dimethylbenzyl ammonium chloride, myristyl picolinium chloride, N-ethyl morpholinium chloride, laurylisoquinolinium bromide, alkyl imidazolinium chloride, benzalkonium chloride, cetyl pyridinium chloride, coconut dimethyl benzyl ammonium chloride, stearyl dimethyl benzyl ammonium chloride, alkyl dimethyl benzyl ammonium chloride, alkyl diethyl benzyl ammonium chloride, alkyl dimethyl benzyl ammonium bromide, di-isobutyl phenoxyethoxyethyl trimethyl ammonium chloride, di-isobutylphenoxyethoxyethyl dimethyl alkyl ammonium chloride, methyldodecylbenzyl trimethyl ammonium chloride, cetyl trimethyl ammonium bromide, octadecyl dimethyl ethyl ammonium bromide, cetyl dimethyl ethyl ammonium bromide, octadec-9-enyl dimethyl ethyl ammonium bromide, dioctyl dimethyl ammonium chloride, dodecyl trimethyl ammonium chloride, octadecyl trimethyl ammonium chloride, octadecyl trimethyl ammonium bromide, hexadecyl trimethyl ammonium iodide, octyl trimethyl ammonium fluoride, and mixtures thereof. Other water dispersible salts, such as the acetates, sulfates, nitrates, and phosphates, are effective in place of the halides, but the chlorides and bromides are preferred. The silicone group is preferably substituted with alkyl ethers. Preferred alkyl ethers are short carbon chain ethers such as methoxy and ethoxy substituents.

Examples of particularly preferred film-forming, organosilicone quaternary ammonium compounds which find use in the present inventive compositions include those which may be represented by the following structural representation:

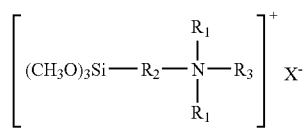

wherein:
R$_1$ and R$_2$ each independently represent short chain alkyl or alkenyl groups, preferably C$_1$-C$_8$ alkyl or alkenyl groups;
R$_3$ represents a C$_{11}$-C$_{22}$ alkyl group; and
X represents a salt forming counterion, especially a halogen.

Preferred short chain alkyl substituents for R$_1$ are methyl and ethyl, preferred short chain alkyl substituents for R$_2$ are straight chain links of methylene groups consisting of from 1 to 4 members, preferred R$_3$ substituents are straight chain links of methylene groups consisting of from 11 to 22 members, and preferred halogens for X are chloride and bromide.

A particularly preferred and commercially available film-forming, organosilicone quaternary ammonium compound useful in the inventive compositions is AEM® 5772 or AEM® 5700 (from Aegis Environmental Co., Midland, Mich.). Both of these materials are described as being 3-(trimethoxysilyl)propyloctadecyldimethyl ammonium chloride, AEM® 5700 and is sold as a 42% by weight active solution of the compound in a water/methanol mixture, while AEM® 5772 is sold as a 72% by weight active solution of the compound in a water/methanol mixture. While the film-forming, organosilicone quaternary ammonium compound may be present in any effective amount, desirably it is present in amounts of from 0.01-10% wt., more desirably from 0.01-5% wt. based on the total weight of the inventive compositions The compositions of the invention are acidic, and exhibit a pH of less than 7, more preferably about 4.5 and less and most preferably from 3-4.5. Whereas the presence of the acid mixture described above will impart acidity to the composition, it is frequently desirable to include a buffer or pH adjusting agent to the compositions to maintain the compositions approximately at a desired pH (or pH range). Exemplary useful pH buffers include inorganic and organic buffering agent, and especially include alkali metal and alkaline earth metal hydroxides such as sodium hydroxide and potassium hydroxide. Others not described here may also be used. Particularly preferred is sodium hydroxide which is widely available at low cost, and is effective in adjusting and buffering the pH of the inventive compositions.

While not an essential feature in all embodiments of the inventive compositions, desirably the liquid compositions of the invention comprise at least one fragrancing agent. Such may be one or more substances or mixtures of substances including those which are naturally derived (i.e., obtained by extraction of flower, herb, blossom or plant), those which are artificially derived or produced (i.e., mixture of natural oils and/or oil constituents), and those which are synthetically produced substances (odiferous substances). In the present invention, the precise composition of the fragrance constituent is of no particular consequence as long as it may be effectively included as a constituent of the compositions, and have a pleasing fragrance. For those compositions which are intended to be used in a domestic environment, the fragrance constituent, as well as the other ingredients used in making up compositions of the invention should be cosmetically acceptable, i.e., feature low toxicity or no toxicity, hypoallergenic character, etc. The fragrance constituent may be included in any effective amount.

As discussed previously, the inventive compositions may comprise one or more conventional optional additives. By way of non-limiting example, these include: pH adjusting agents and pH buffers including organic and inorganic salts, fragrancing, optical brighteners, coloring agents such as dyes and pigments, opacifying agents, hydrotropes, anti-foaming agents, anti-spotting agents, anti-oxidants, anti-corrosion agents as well as others not specifically elucidated here. These ingredients may be present in any combinations and in any suitable amount that is sufficient for imparting the desired properties to the compositions. These one or more conventional additives, when present, should be present in minor amounts, preferably in total comprise less than about 5% by weight (on an active weight basis) of the compositions, and desirably less than about 3% wt.

Such materials as described above are each individually known to the art, many of which are described in *McCutcheon's Emulsifiers and Detergents* (Vol. 1), *McCutcheon's Functional Materials* (Vol. 2), North American Edition, 1991; *Kirk-Othmer, Encyclopedia of Chemical Technology*, 3rd Ed., Vol. 22, the contents of which are herein incorporated by reference For any particular composition described above, any optional ingredients should be compatible with the other ingredients present.

As is noted above, the compositions according to the invention are aqueous in nature. Water is added to order to provide to 100% by weight of the compositions of the invention. The water may be tap water, but is preferably distilled and is most preferably deionized water. If the water is tap water, it is preferably substantially free of any undesirable impurities such as organics or inorganics, especially minerals salts which are present in hard water which may thus undesirably interfere with the operation of the constituents present in the aqueous compositions according to the invention.

The compositions may be made by simply mixing measured amounts of the individual constituents into water, at room temperature under constant stirring until a homogenous mixture is attained. In a preferred method, a first premixture is made by mixing together the nonionic and fragrance constituents. A second premixture is made by mixing the water, cellulose thickener and optionally, sodium hydroxide to form a homogeous mixture. Thereafter, the first premixture is added to the second premixture, after which the remaining constituents are added, and mixing continues until a homogenous mixture is attained.

According to certain preferred embodiments of the invention there are provided thickened aqueous acidic hard surface cleaning and disinfecting compositions which consist essentially of:

0.1-10% wt. of one or more nonionic surfactants, particularly linear primary alcohol ethoxylates;
01.-3% wt. one or more quaternary ammonium surfactant compounds having germicidal properties;
0.1-15% wt. of an acid constituent based on one or more water soluble organic acids, particularly water soluble organic acids selected from the group consisting of: formic acid, citric acid, mixtures of formic acid with citric acid, and oxalic acid;
0.1-5% wt. a cellulose based thickening composition;
0.01-5% wt. a film-forming, organosilicone quaternary ammonium compound;
up to 10% wt. of one or more of a pH adjusting agent, fragrance, coloring agent;
and, water.

Most especially preferred are one or more of the compositions described with reference to the Examples, following.

The thickened aqueous acidic hard surface cleaning and disinfecting composition according to the invention is desirably provided as a ready to use product which may be directly applied to a hard surface. By way of example, hard surfaces include surfaces composed of refractory materials such as: glazed and unglazed tile, brick, porcelain, ceramics as well as stone including marble, granite, and other stones surfaces; glass; metals; plastics e.g. polyester, vinyl; fiberglass, Formica®, Corian® and other hard surfaces known to the industry. Hard surfaces which are to be particularly denoted include those associated with kitchen environments and other environments associated with food preparation. The inventive compositions are particularly useful in cleaning and disinfecting lavatory fixtures such as shower stalls, bathtubs and bathing appliances (racks, curtains, shower doors, shower bars) toilets, bidets, wall and flooring surfaces especially those which include refractory materials and the like. The inventive compositions especially particularly useful in the cleaning and disinfecting of lavatory fixtures, especially toilets and bidets. They may be packaged in any suitable container particularly flasks or bottles, including squeeze-type bottles, as well as bottles provided with a spray apparatus which is used to dispense the composition by spraying.

The following examples below illustrate exemplary and preferred formulations of the concentrate composition according to the instant invention. It is to be understood that these examples are presented by means of illustration only and that further useful formulations fall within the scope of this invention and the claims may be readily produced by one skilled in the art and not deviate from the scope and spirit of the invention.

Throughout this specification and in the accompanying claims, weight percents of any constituent are to be understood as the weight percent of the active portion of the referenced constituent, unless otherwise indicated.

EXAMPLES

The following examples illustrate the formulation and performance of various compositions of the invention, as well as certain particularly preferred embodiments of the invention.

Exemplary formulations illustrating certain preferred embodiments of the inventive compositions and described in more detail in Table 1 below were formulated generally in accordance with the following protocol. The weight percentages indicated weights of the named chemical compounds which were supplied either as "neat" compositions (100% wt. active) or as dilutions, typically as aqueous or aqueous/alcoholic dilutions at concentrations less than "100% actives".

TABLE 1

| | Ex. 1 | Ex. 2 | Ex. 3 | Ex. 4 | Ex. 5 | Ex. 6 | Ex. 7 | Ex. 8 |
|---|---|---|---|---|---|---|---|---|
| hydroxyethylcellulose | 0.52 | 0.45 | 0.45 | 0.45 | 0.45 | 0.45 | 0.45 | 0.45 |
| 3-(trimethoxysilyl)propyloctadecyldimethyl ammonium chloride | 0.04 | 0.04 | 0.04 | 0.04 | 0.04 | 0.04 | 0.04 | 0.04 |
| quaternary ammonium[1] | 1.4 | 0.36 | 0.36 | 0.36 | 0.36 | 0.36 | 0.36 | 0.36 |
| alcohol ethoxylate[3] | — | 0.30 | 0.30 | 0.30 | 0.30 | 0.30 | 0.30 | 0.30 |
| alcohol ethoxylate[4] | 0.75 | — | — | — | — | — | — | — |
| alcohol ethoxylate[5] | — | — | — | — | — | — | — | — |
| formic acid | — | 1.17 | 1.17 | 1.17 | 1.17 | 1.17 | 1.17 | 1.17 |
| citric acid | — | 1.0 | 1.0 | 1.0 | 1.0 | 1.0 | 1.0 | 1.0 |
| oxalic acid | 7.69 | — | — | — | — | — | — | — |
| sodium hydroxide[7] | — | 2.02 | 2.04 | 2.04 | 2.04 | 2.04 | 2.04 | 2.04 |
| sodium hydroxide[8] | 1.0 | — | — | — | — | — | — | — |
| preservative | — | 0.0041 | 0.0041 | 0.0041 | 0.0041 | 0.0041 | 0.0041 | 0.0041 |
| fragrance | 0.28 | 0.21 | 0.21 | 0.21 | 0.21 | 0.21 | 0.21 | 0.21 |
| dye - yellow 94 | — | 1.0 | 0.612 | 0.245 | — | — | 1.60 | — |
| dye - yellow 17 | 0.16 | — | — | — | — | — | — | — |
| dye - yellow 36 | — | — | — | — | — | 0.184 | — | — |
| dye - yellow 232 | — | — | — | — | — | — | — | — |
| dye - blue 80 | — | — | 0.064 | 0.495 | 0.75 | — | — | — |
| dye - blue 9 | — | — | — | — | — | 0.576 | — | 0.80 |
| dye - blue 7 | 0.25 | — | — | — | — | — | — | — |
| di water | q.s. | q.s. | q.s. | q.s. | q.s. | q.s. | q.s. | q.s. |
| final pH | 4.2 | 4.2 | 4.2 | 4.2 | 4.2 | 4.2 | 4.2 | 4.2 |

| | Ex. 9 | Ex. 10 | Ex. 11 | Ex. 12 | Ex. 13 | Ex. 14 | Ex. 15 | Ex. 16 |
|---|---|---|---|---|---|---|---|---|
| hydroxyethylcellulose | 0.45 | 0.5 | 0.45 | 0.45 | 0.45 | 0.45 | 0.52 | 0.45 |
| 3-(trimethoxysilyl)propyloctadecyldimethyl ammonium chloride | 0.04 | 0.35 | 0.20 | 0.28 | 0.02 | 0.04 | 0.04 | 0.03 |
| quaternary ammonium[1] | 0.36 | 0.36 | 0.30 | 0.30 | 0.30 | 0.30 | — | 0.30 |
| quaternary ammonium[2] | — | — | — | — | — | — | 1.4 | — |
| alcohol ethoxylate[3] | 0.30 | — | 0.30 | 0.30 | 0.30 | 0.30 | — | 0.30 |
| alcohol ethoxylate[4] | — | — | — | — | — | — | — | — |
| alcohol ethoxylate[5] | — | 0.6 | — | — | — | — | — | — |
| alcohol ethoxylate[6] | — | — | — | — | — | — | 0.75 | — |
| formic acid | 1.17 | 1.17 | 1.16 | 1.17 | 1.17 | 1.17 | — | 1.17 |
| citric acid | 1.4 | 1.0 | 1.0 | 1.0 | 1.0 | — | 1.00 | 1.0 |
| oxalic acid | — | — | — | — | — | — | 7.69 | — |
| sodium hydroxide[7] | 2.04 | 2.31 | 2.03 | 2.03 | 2.03 | 2.03 | 1.0 | 2.03 |
| sodium hydroxide[8] | — | — | — | — | — | — | — | — |
| preservative | 0.0041 | — | 0.0041 | 0.0041 | 0.0041 | 0.0041 | — | 0.0041 |
| fragrance | 0.21 | 0.28 | 0.21 | 0.21 | 0.21 | 0.21 | 0.28 | 0.21 |
| dye - yellow 94 | 0.408 | 1.0 | — | 1.0 | 1.0 | 1.0 | — | 1.0 |
| dye - yellow 17 | — | — | — | — | — | — | 0.16 | — |
| dye - yellow 36 | — | — | — | — | — | — | — | — |
| dye - yellow 232 | — | — | 0.18 | — | — | — | — | — |
| dye - blue 80 | — | — | — | — | — | — | — | — |
| dye - blue 9 | 0.765 | — | 0.58 | — | — | — | — | — |
| dye - blue 7 | — | — | — | — | — | — | 0.25 | — |
| di water | q.s. | q.s. | q.s. | q.s. | q.s. | q.s. | q.s. | q.s. |
| final pH | TA 4.2 | — | — | — | — | — | — | — |

As is indicated, to all of the formulations of Table 1 was added sufficient deionized water in "quantum sufficient" to provide 100 parts by weight of a particular formulation.

The identity of the constituents of used to produce various formulations described herein are disclosed on Table 2, below, including the "actives" percentage of each were a constituent was not 100% wt. "actives".

TABLE 2

| | |
|---|---|
| 3-(trimethoxysilyl)propyloctadecyldimethyl ammonium chloride | AEM 5772 (72%) ex. Aegis Environmental |
| quaternary ammonium[1] | BTC 8358 (80%) ex. Stepan Co. |
| quaternary ammonium[2] | BARDAC 208M (80%) ex. Lonza |
| alcohol ethoxylate[3] | EMPILAN KB-10 (100%) ex. Albright & Wilson |
| alcohol ethoxylate[4] | NEODOL 25-9 (100%) ex. Shell Co. |
| alcohol ethoxylate[5] | GENAPOL 26-L-80 (100%) ex. Clariant |
| alcohol ethoxylate[6] | TOMADOL 25-9, linear primary C12-C15 alcohol ethoxylates, avg. 8.9 mols ethylene oxide(100%) ex. Shell co. |
| formic acid | formic acid (94%) ex BASF |
| citric acid | citric acid, anhydrous (100%) ex ADM |
| oxalic acid | oxalic acid, (6.5%) ex. VWR |
| hydroxyethylcellulose | CELLOSIZE QP100MH (100%) ex. Union Carbide |
| sodium hydroxide[7] | sodium hydroxide (50%) |
| sodium hydroxide[8] | sodium hydroxide (25%) |
| preservative | ACTICIDE MBS (2.35-2.65% 1,2-methyl-4-isothiazolin-3-one, and 2.35-2.65% benzisothiazolin-3-one) ex. ACTI-Chem |

TABLE 2-continued

| | |
|---|---|
| dye - yellow 94 | 1% aqueous solution of Acid Yellow 94 (100%) ex. BASF |
| dye - yellow 17 | 1% aqueous solution of Acid Yellow 17 ex. Crompton & Knowles |
| dye - yellow 36 | 1% aqueous solution of Acid Yellow 17 |
| dye - blue 80 | 1% aqueous solution of Acid Blue 80 (100%) ex. Ciba |
| dye - blue 9 | 1% aqueous solution of Acid Blue 9 (50%) ex. BASF |
| dye - blue 7 | 1% aqueous solution of Acid Blue 7 ex. Crompton & Knowles |
| fragrance | proprietary composition |
| di water | deionized water |

Surface Protection

The efficacy of compositions according to the invention to resist the buildup of limescale was evaluated against several commercially available products, as well as against a control wherein no treatment composition was used.

Nine black ceramic toilets were used in the test. Two toilets were treated using a formulation according to Example 2 described on Table 1. Four further toilets were evaluated using a commercially available toilet cleaning products, two toilets were treated with VIAKAL (ex. Procter & Gamble Co.) and two further toilets were treated with CLOROX with TEFLON (ex. Clorox Co.) The last, ninth toilet was not treated, nor was it flushed for the duration of the test.

Each of the nine toilets was first prepared by first cleaning with LYSOL toilet bowl cleaner followed by rinsing with acetone. Each of the toilets were flushed once to wet the inner walls of the toilet bowl. Like amount of each product was applied from squeeze bottles to the toilets and allowed to remain on the surface of the toilets, without scrubbing of other manual agitation for 15 minutes, and thereafter the flushing protocol was initiated.

The toilets were flushed 10 times per day at one-hour intervals, for a total duration of 15 days thereby ensuring 150 flushes for toilet, except for the ninth toilet which was not flushed for the duration of the test.

Following the conclusion of the 150 flushes, the bowls of each of the nine toilets was drained of water and allowed to air-dry prior to the visual evaluations by 20 panelists who were asked to both rank the toilets for least visible buildup of limescale within the toilet bowl particularly at the waterline, and to also rate the overall cleanliness of each of the toilet bowls. The identity of the formulations used in each of the toilet bowls was not disclosed to the panelists, nor that two toilet bowls were treated with each formulation. The results are indicated on the following Tables A and B:

TABLE A

| | Panelist | | | | | | | | | | | | | | | | | | | |
|---|---|---|---|---|---|---|---|---|---|---|---|---|---|---|---|---|---|---|---|---|
| Rank# | 1 | 2 | 3 | 4 | 5 | 6 | 7 | 8 | 9 | 10 | 11 | 12 | 13 | 14 | 15 | 16 | 17 | 18 | 19 | 20 |
| 1st | E2 | E2 | E2 | E2 | E1 | E2 | E2 | E1 | E1 | E2 | E1 | E1 | E1 | E1 | E1 | E2 | E1 | E2 | E1 | E1 |
| 2nd | E1 | E1 | E1 | E1 | E2 | E1 | E1 | E2 | E2 | U1 | U1 | U1 | E2 | V2 | V2 | U1 | V2 | E1 | V2 | E2 |
| 3rd | V2 | V2 | U1 | V2 | V2 | V2 | U2 | V2 | U1 | E1 | E2 | V2 | E2 | E2 | E1 | E2 | U1 | E2 | V2 |
| 4th | U1 | U1 | V2 | U1 | U1 | C1 | U1 | U2 | V2 | C2 | C2 | V2 | U1 | U1 | U1 | V2 | U1 | V2 | U1 | U1 |
| 5th | C2 | V1 | C2 | C2 | V1 | U1 | C1 | U1 | C1 | U2 | V1 | C1 | V1 | C1 | C2 | C2 | V1 | V1 | C1 | C1 |
| 6th | C1 | C1 | C1 | V1 | C1 | V1 | C2 | C2 | V1 | V1 | C1 | V1 | C2 | V1 | V1 | V1 | C1 | C1 | V1 | V1 |
| 7th | V1 | C2 | V1 | C1 | C2 | C2 | V1 | C1 | C2 | C1 | V2 | C2 | U2 | C2 | C1 | C1 | C2 | C2 | C2 | C2 |
| 8th | U2 | U2 | U2 | U2 | U2 | U2 | V2 | V1 | U2 | V2 | U2 | U2 | C1 | U2 | U2 | U2 | U2 | U2 | U2 | U2 |

V1 = 1st toilet treated with VIAKAL,
V2 = 2nd toilet treated with VIAKAL
C1 = 1st toilet treated with CLOROX with TEFLON,
C2 = 2nd toilet treated with CLOROX with TEFLON
E1 = 1st toilet treated with Ex. 2 formulation,
E2 = 2nd toilet treated with Ex. 2 formulation
U1 = 1st untreated toilet,
U2 = 2nd untreated toilet
On Table A, rank order assigned by each panelist to based on least visible buildup of limescale within the toilet bowl particularly at the waterline.

TABLE B

| Formulation tested: | Panelist | | | | | | | | | | | | | | | | | | | | | |
|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | average |
| VIAKAL(1) | 5 | 5 | 7 | 5 | 1 | 1 | 5 | 7 | 4 | 4 | 6 | 3 | 4 | 2 | 2 | 2 | 5 | 2 | 5 | 3 | 3.90 |
| CLOROX(1) | 7 | 5 | 7 | 4 | 2 | 2 | 4 | 8 | 5 | 6 | 6 | 2 | 5 | 3 | 2 | 5 | 5 | 2 | 7 | 3 | 4.50 |
| EX.2(1) | 8 | 7 | 8 | 8 | 8 | 9 | 7 | 9 | 4 | 7 | 8 | 4 | 7 | 6 | 8 | 7 | 6 | 8 | 8 | 6 | 7.15 |
| VIAKAL(2) | 5 | 6 | 8 | 7 | 2 | 8 | 6 | 8.5 | 3 | 5 | 6 | 4 | 3 | 2 | 5 | 1 | 3 | 6 | 7 | 5 | 5.03 |
| UNTREATED(1) | 4 | 8 | 8 | 7 | 2 | 5 | 5 | 8.5 | 6 | 3 | 7 | 4 | 6 | 1 | 3 | 4 | 4 | 2 | 6 | 4 | 4.78 |
| UNTREATED(2) | 5 | 3 | 6 | 4 | 1 | 1 | 3 | 6 | 3 | 1 | 5 | 3 | 2 | 2 | 1 | 1 | 4 | 1 | 4 | 1 | 2.85 |
| CLOROX(2) | 4 | 4 | 6 | 4 | 1 | 2 | 4 | 6 | 3 | 2 | 6 | 4 | 5 | 2 | 2 | 2 | 5 | 2 | 5 | 2 | 3.55 |
| EX.2(2) | 8 | 7 | 9 | 7 | 8 | 8 | 7 | 8.5 | 8 | 8 | 8 | 8 | 7 | 6 | 8 | 9 | 6 | 7 | 8 | 6 | 7.58 |

On Table B, overall cleanliness of each of the toilet bowls with rating assigned by each of the twenty panelists, using an scale of 1-9, wherein 1 = not at all clean, 5 = moderately clean, 9 = extremely clean. Table B also indicates the numerical average for each of the formulations tested, based on the scored assigned by the twenty panelists.

Evaluation of Antimicrobial Efficacy:

A formulation according to the invention as described as Example 2 from Table 1 was evaluated in order to evaluate its antimicrobial efficacy against *Staphylococcus aureus* (ATCC 6538), *Escherichia coli* (ATCC 10536), *Pseudomonas aeruginosa* (ATCC 15442) and *Enterococcus hirae* (ATCC 10541). The testing was performed on ten (10) substrates generally in accordance with the protocols outlined in "Use-Dilution Method", Protocols 955.14, 955.15 and 964.02 described in Chapter 6 of "Official Methods of Analysis", 16$^{th}$ Edition, of the Association of Official Analytical Chemists; "Germicidal and Detergent Sanitizing Action of Disinfectants", 960.09 described in Chapter 6 of "Official Methods of Analysis", 15$^{th}$ Edition, of the Association of Official Analytical Chemists, or American Society for Testing and Materials (ASTM) E 1054-91 the contents of which are herein incorporated by reference. This test is also commonly referred to as the "AOAC Use-Dilution Test Method". The formulation was tested without further dilution for a 60 minute contact time according to the protocols of the AOAC Use-Dilution Test Method.

As is appreciated by the skilled practitioner in the art, the results of the AOAC Use-Dilution Test Method indicates the number of test substrates wherein the tested organism remains viable after contact for 10 minutes with a test disinfecting composition/total number of tested substrates (cylinders) evaluated in accordance with the AOAC Use-Dilution Test. Thus, a result of "0/10" indicates that of 10 test substrates bearing the test organism and contacted for 10 minutes in a test disinfecting composition, 0 test substrates had viable (live) test organisms at the conclusion of the test. Such a result for each of the tested organism is excellent, illustrating the excellent disinfecting efficacy of the tested composition. Results of the antimicrobial testing of the formulation are indicated on the following table. The reported results indicate the number of test cylinders with live test organisms/number of test cylinders tested for each example formulation and organism tested.

TABLE 3

| Staphylococcus aureus | 0/10 |
| Escherichia coli | 0/10 |
| Pseudomonas aeruginosa | 0/10 |
| Enterococcus hirae | 0/10 |

As may be seen from the results indicated above, the compositions according to the invention provide excellent disinfection of hard surfaces.

A formulation according to the invention as described as Example 2 from Table 1 was also evaluated in order to evaluate its antimicrobial efficacy against *Staphylococcus aureus* (ATCC 6538), *Escherichia coli* (ATCC 10536), *Pseudomonas aeruginosa* (ATCC 15442) and *Enterococcus hirae* (ATCC 10541 in accordance with the protocols of British Standard EN 1276, a quantitative suspension test for the evaluation of bactericidal activity of chemical disinfectants and antiseptics used in food, industrial, domestic and institutional environments—Test Method and requirements (phase 2, step 1) Ref. No. EN 1276: 1997E the contents of which are herein incorporated by reference. The protocols of this test were followed with the following variations from the published protocol: the formulation was tested only for a 60 minute contact time; the test plates were incubated for 2 nights, and left at ambient temperature a third night, at which time results were read and recorded; and, a final concentration of 3 g/l bovine albumin was used in testing for dirty conditions (Section 5.2.2.8.2, part b). A specified in the protocol of British Standard EN 1276 a reduction in viability was calculated for each test system, and at least two test systems were evaluated for each of the microorganisms. The results of this test per the British Standard EN 1276 is reported on the following Table.

| Test System | Plate Count | Treatment Tube Recovery | Treatment Tube Recovery Average | Reduction in Viability | Test Result |
|---|---|---|---|---|---|
| S. aureus #1a | 0 | <1.5 × 10$^2$ | <1.5 × 10$^2$ | >2.75 × 10$^5$ | PASS |
| S. aureus #1b | 0 | <1.5 × 10$^2$ | | | |
| S. aureus #2a | 0 | <1.5 × 10$^2$ | <1.5 × 10$^2$ | >2.75 × 10$^5$ | PASS |
| S. aureus #2b | 0 | <1.5 × 10$^2$ | | | |
| E. coli #1a | 0 | <1.5 × 10$^2$ | <1.5 × 10$^2$ | >1.37 × 10$^5$ | PASS |
| E. coli #1b | 0 | <1.5 × 10$^2$ | | | |
| E. coli #2a | 0 | <1.5 × 10$^2$ | <1.5 × 10$^2$ | >1.37 × 10$^5$ | PASS |
| E. coli #2b | 0 | <1.5 × 10$^2$ | | | |
| Ps. aeruginosa #1a | 0 | <1.5 × 10$^2$ | <1.5 × 10$^2$ | >2.25 × 10$^5$ | PASS |
| Ps. aeruginosa #1b | 0 | <1.5 × 10$^2$ | | | |
| Ps. aeruginosa #2a | 0 | <1.5 × 10$^2$ | <1.5 × 10$^2$ | >2.25 × 10$^5$ | PASS |
| Ps. aeruginosa #2b | 0 | <1.5 × 10$^2$ | | | |
| E. hirae #1a | 0 | <1.5 × 10$^2$ | <1.5 × 10$^2$ | >1.81 × 10$^5$ | PASS |
| E. hirae #1b | 0 | <1.5 × 10$^2$ | | | |
| E. hirae #2a | 0 | <1.5 × 10$^2$ | <1.5 × 10$^2$ | >1.81 × 10$^5$ | PASS |
| E. hirae #2b | 0 | <1.5 × 10$^2$ | | | |

As may be seen from the results indicated above, the compositions according to the invention provide excellent disinfection of hard surfaces.

While the invention is susceptible of various modifications and alternative forms, it is to be understood that specific embodiments thereof have been shown by way of example in the drawings which are not intended to limit the invention to the particular forms disclosed; on the contrary the intention is to cover all modifications, equivalents and alternatives falling within the scope and spirit of the invention as expressed in the appended claims.

The invention claimed is:

1. Thickened aqueous acidic hard surface cleaning and disinfecting composition with film forming properties which comprises:

0.1-10% wt. of one or more nonionic surfactants;
   0.1-3% wt. of one or more quaternary ammonium surfactant compounds having germicidal properties;
   0.1-15% wt. of an acid constituent based on one or more water soluble organic acids, particularly water soluble organic acids selected from the group consisting of formic acid, citric acid, mixtures of formic acid with citric acid, and oxalic acid;
   0.1-5% wt. of a cellulose based thickening composition;
   0.01-5% wt. of a film-forming, organosilicone quaternary ammonium compound;
   up to 10% wt. of one or more of a pH adjusting agent, fragrance/perfume, or coloring agent;
   optionally, one or more further conventional constituents selected from the group consisting of pH buffering agents, perfume carriers, hydrotropes, additional germicides, fungicides, anti-oxidants, and anti-corrosion agents;
   and, water.

2. The composition according to claim 1 wherein the acid constituent consists solely of oxalic acid.

3. The composition according to claim 1 wherein the acid constituent consists solely of a mixture of citric acid and formic acid.

4. The composition according to claim 1 wherein the one or more nonionic surfactants are linear primary alcohol ethoxylates.

5. A composition according to claim 1 wherein the organosilicone quaternary ammonium compounds are those which may be represented by the following structural representation:

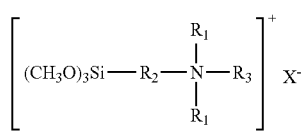

wherein:
$R_1$ and $R_2$ each independently represent short chain alkyl or alkenyl groups, preferably $C_1$-$C_8$ alkyl or alkenyl groups;
$R_3$ represents a $C_{11}$-$C_{22}$ alkyl group; and
X represents a salt forming counterion, especially a halogen.

6. A composition according to claim 1 wherein the composition exhibits a pH of less than about 4.5.

7. Thickened aqueous acidic hard surface cleaning and disinfecting composition with film forming properties which consists essentially of:
 0.1-10% wt. of one or more nonionic surfactants;
 0.1-3% wt. of one or more quaternary ammonium surfactant compounds having germicidal properties;
 0.1-15% wt. of an acid constituent based on one or more water soluble organic acids, particularly water soluble organic acids selected from the group consisting of formic acid, citric acid, mixtures of formic acid with citric acid, and oxalic acid;
 0.1-5% wt. of a cellulose based thickening composition;
 0.01-5% wt. of a film-forming, organosilicone quaternary ammonium compound;
 up to 10% wt. of one or more of a pH adjusting agent, fragrance/perfume, or coloring agent;
 optionally, one or more further conventional constituents selected from the group consisting of pH buffering agents, perfume carriers, hydrotropes, additional germicides, fungicides, anti-oxidants, and anti-corrosion agents;
 and, water.

8. A composition according to claim 7 wherein the one or more water soluble organic acids are selected from the group consisting of: formic acid, citric acid, mixtures of formic acid with citric acid, and oxalic acid.

9. The composition according to claim 7 wherein the acid constituent consists solely of oxalic acid.

10. The composition according to claim 7 wherein the acid constituent consists solely of a mixture of citric acid and formic acid.

11. A composition according to claim 7 wherein the organosilicone quaternary ammonium compounds are those which may be represented by the following structural representation:

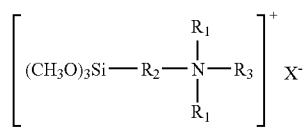

wherein:
$R_1$ and $R_2$ each independently represent short chain alkyl or alkenyl groups, preferably $C_1$-$C_8$ alkyl or alkenyl groups;
$R_3$ represents a $C_{11}$-$C_{22}$ alkyl group; and
X represents a salt forming counterion, especially a halogen.

12. A composition according to claim 7 wherein the composition exhibits a pH of less than about 4.5.

13. A method for cleaning and disinfecting hard surfaces, preferably metal, enamel and porcelain surfaces as found on lavatory fixtures, which method comprises the step of:
 applying a cleaning and/or disinfecting effective amount of the compositions according to claim 1 to a surface in need of treatment.

14. A method for providing a residual film on surfaces which aids in limiting or preventing further limescale deposition on such hard surfaces, which method includes step of:
 composition according to claim 1.

* * * * *

UNITED STATES PATENT AND TRADEMARK OFFICE
CERTIFICATE OF CORRECTION

| | | |
|---|---|---|
| PATENT NO. | : 7,304,022 B2 | Page 1 of 1 |
| APPLICATION NO. | : 10/577093 | |
| DATED | : December 4, 2007 | |
| INVENTOR(S) | : Cheung et al. | |

It is certified that error appears in the above-identified patent and that said Letters Patent is hereby corrected as shown below:

Column 16, line 46, "composition according to claim 1" should read --applying a residual film forming effective amount of the composition according to claim 1 to a surface in need of treatment.--

Signed and Sealed this

Sixteenth Day of December, 2008

JON W. DUDAS
*Director of the United States Patent and Trademark Office*